(12) United States Patent
James et al.

(10) Patent No.: US 11,730,686 B2
(45) Date of Patent: Aug. 22, 2023

(54) COSMETIC SKINCARE COMPOSITIONS

(71) Applicant: THE BOOTS COMPANY PLC, Nottingham (GB)

(72) Inventors: Leanne Marie James, Leicestershire (GB); Clare Helena O'Connor, Derbyshire (GB)

(73) Assignee: THE BOOTS COMPANY PLC, Nottingham (GB)

( * ) Notice: Subject to any disclaimer, the term of this patent is extended or adjusted under 35 U.S.C. 154(b) by 0 days.

(21) Appl. No.: 16/490,221

(22) PCT Filed: Feb. 28, 2018

(86) PCT No.: PCT/EP2018/025050
§ 371 (c)(1),
(2) Date: Aug. 30, 2019

(87) PCT Pub. No.: WO2018/157975
PCT Pub. Date: Sep. 7, 2018

(65) Prior Publication Data
US 2020/0069546 A1    Mar. 5, 2020

(30) Foreign Application Priority Data
Mar. 1, 2017 (EP) .................................. 17020082

(51) Int. Cl.
| | | |
|---|---|---|
| A61K 8/41 | (2006.01) | |
| A61K 8/9789 | (2017.01) | |
| A61Q 17/04 | (2006.01) | |
| A61P 17/02 | (2006.01) | |
| A61K 8/97 | (2017.01) | |
| A61Q 17/00 | (2006.01) | |
| A61K 8/68 | (2006.01) | |

(52) U.S. Cl.
CPC .............. *A61K 8/41* (2013.01); *A61K 8/9789* (2017.08); *A61Q 17/04* (2013.01); *A61K 2800/522* (2013.01)

(58) Field of Classification Search
CPC .. A61K 8/41; A61K 8/9789; A61K 2800/522; A61K 8/97; A61Q 17/04; A61Q 17/00; A61P 17/02
See application file for complete search history.

(56) References Cited

U.S. PATENT DOCUMENTS

2006/0018866 A1    1/2006  Kawakami et al.

FOREIGN PATENT DOCUMENTS

| DE | 19824727 A1 | 12/1999 |
|---|---|---|
| EP | 2857000 A1 | 4/2015 |
| EP | 3069763 A1 | 9/2016 |
| JP | 2006062968 A | 3/2006 |

(Continued)

OTHER PUBLICATIONS

Aburjai T et al: "Plants used in cosmetics", Phytotherapy Research, John Wiley & Sons Ltd. Chichester, GB, vol. 17, No. 9, Nov. 1, 2003 (Nov. 1, 2003), pp. 987-1000, XP002327682, ISSN: 0951-418X, DOI: 10.1002/PTR.1363.

(Continued)

*Primary Examiner* — Trevor Love
(74) *Attorney, Agent, or Firm* — Marshall, Gerstein & Borun LLP

(57) ABSTRACT

According to the present invention there is provided a cosmetic composition comprising: (i) a polyphenolic antioxidant agent; and (ii) a sphingosine compound.

4 Claims, 4 Drawing Sheets

(56) References Cited

FOREIGN PATENT DOCUMENTS

| KR | 20070098078 A | 10/2007 |
| KR | 20150011644 A | 2/2015 |
| WO | WO-2009/063068 A1 | 5/2009 |

OTHER PUBLICATIONS

International Rosacea Foundation: "Non-Prescription Treatments for Rosacea", Internet Citation, May 31, 2009 (May 31, 2009), XP007917401, Retrieved from the Internet: URL:http://replay.waybackmachine.org/20090531050612/http://www.internationalrosaceafoundation.org/nonprescription_1.php4 [retrieved on Mar. 2, 2011].
International Preliminary Reporton Patentability, corresponding International Application No. PCT/EP2018/025050, dated Jun. 17, 2019.
International Search Report and Written Opinion, corresponding International Application No. PCT/EP2018/025050, dated Jun. 18, 2018.
Office Action for corresponding Korean Patent Application No. 10-2019-7028064, dated Feb. 23, 2021 (English Translation).

Figure 1a

| Material Name | Example formulations (%w/w) | | | | |
| --- | --- | --- | --- | --- | --- |
| | 1 | 2 | 3 | 4 | 5 |
| Sequestrene NA4 | 0.025 | 0.05 | 0.01 | 0.01 | 0.01 |
| Glycerin BP | 2 | 0 | 0 | 0 | 7 |
| Keltrol RD | 0.1 | 0.3 | 1 | 1 | 0.5 |
| Aristoflex AVC | 1.6 | 0.7 | 1.5 | 1.5 | 1.5 |
| DRY FLO PC | 2 | 3 | 5 | 5 | 5 |
| 1,3-BUTYLENE GLYCOL | 0 | 3 | 0 | 0 | 0 |
| TWEEN 20 | 0.4 | 0.2 | 0.8 | 0.8 | 0.8 |
| Dimethicone+dimethicone crosspolymer | 6 | 4 | 10 | 10 | 0 |
| PURIFIED WATER BP | 80.261 | 83.21 | 74.3775 | 74.3868 | 79.837 |
| Perf Comp 30024992 HA Drom | 0.35 | 0.1 | 0.5 | 0.5 | 0.5 |
| Phenoxetol Nipa | 0.6 | 0.3 | 0.5 | 0.5 | 0.5 |
| Capryly glycol and ethylhexylglycerin | 0.14 | 0.2 | 0.1 | 0.1 | 0.1 |
| D-Panthenol 75L | 0 | 0 | 0 | 0 | 0 |
| Bisabolol | 0.15 | 0 | 0 | 0 | 0 |
| Ascorbyl glucoside | 0 | 0 | 0 | 0 | 0 |
| DL-A-tocopheryl acetate | 0 | 0 | 0 | 0 | 0 |
| Dimethlymethoxy Chromanol | 0 | 0.03 | 0 | 0 | 0 |
| Denatured ethanol B GDE 100% | 0 | 0 | 1 | 1 | 0 |
| Herb ext ophiopogon japonicus root | 0 | 0 | 0 | 0 | 0 |
| Sphinganine | 0.2 | 0.3 | 0 | 0 | 0 |
| Sodium hyaluronate 700-1000 KDA | 0 | 0 | 1 | 1 | 0 |
| Sodium benzoate bp | 0.17 | 0.1 | 0.2 | 0.2 | 0.2 |
| Caustic potash sol'n | 0 | 0 | 0 | 0 | 0 |
| Herb ext camellia sinensis leaf | 0.001 | 0.01 | 0.01 | 0.0012 | 0.003 |
| EUTANOL G | 4 | 3.5 | 3.5 | 3.5 | 3.5 |
| CITRIC ACID MONOHYDRATE BP GRAN | 0 | 0 | 0 | 0 | 0 |
| Dimethicone/Dimethiconol | 2 | 1 | 0 | 0 | 0 |
| Ginkgo Biloba leaf extract | 0.003 | 0 | 0.0025 | 0.002 | 0 |
| Phytosphingosine | 0 | 0 | 0.5 | 0.5 | 0.55 |
| Monoammonium glycyrrhizate | 0 | 0 | 0 | 0 | 0 |
| Shea butter | 0 | 0 | 0 | 0 | 0 |
| Isononyl Isononoate | 0 | 0 | 0 | 0 | 0 |
| Carnauba wax | 0 | 0 | 0 | 0 | 0 |
| Biosaccharide gum | 0 | 0 | 0 | 0 | 0 |

Figure 1b

| Material Name | Example formulations (cont) (%w/w) | | | | |
|---|---|---|---|---|---|
| | 6 | 7 | 8 | 9 | 10 |
| Sequestrene NA4 | 0.03 | 0.03 | 0.03 | 0.03 | 0.03 |
| Glycerin BP | 2 | 0 | 0 | 0 | 0 |
| Keltrol RD | 1 | 1 | 1 | 1 | 0.5 |
| Aristoflex AVC | 2 | 1.5 | 2 | 2 | 1.5 |
| DRY FLO PC | 2 | 2 | 2 | 2 | 3 |
| 1,3-BUTYLENE GLYCOL | 0 | 0 | 0 | 0 | 0 |
| TWEEN 20 | 0.5 | 0.4 | 0.5 | 0.5 | 0.25 |
| Dimethicone+dimethicone crosspolymer | 0 | 0 | 0 | 0 | 0 |
| PURIFIED WATER BP | 86.3855 | 86.3961 | 86.317 | 85.4885 | 83.8185 |
| Perf Comp 30024992 HA Drom | 0.3 | 0.15 | 0.3 | 0.3 | 0.1 |
| Phenoxetol Nipa | 0.2 | 0.6 | 0.2 | 0.2 | 0.7 |
| Capryly glycol and ethylhexylglycerin | 0.3 | 0.3 | 0.3 | 0.3 | 0.4 |
| D-Panthenol 75L | 0 | 0 | 0.5 | 0 | 0.6 |
| Bisabolol | 0 | 0 | 0 | 0.4 | 0 |
| Ascorbyl glucoside | 0 | 0 | 0 | 0 | 0 |
| DL-A-tocopheryl acetate | 0 | 0 | 0 | 0 | 0 |
| Dimethlymethoxy Chromanol | 0 | 0 | 0 | 0 | 0 |
| Denatured ethanol B GDE 100% | 1 | 1 | 1 | 1 | 0 |
| Herb ext ophiopogon japonicus root | 0 | 0 | 0 | 0 | 0 |
| Sphinganine | 0 | 0.11 | 0.15 | 0 | 0.4 |
| Sodium hyaluronate 700-1000 KDA | 0 | 0 | 0 | 0 | 0 |
| Sodium benzoate bp | 0.2 | 0.21 | 0.2 | 0.2 | 0.2 |
| Caustic potash sol'n | 0 | 0 | 0 | 0 | 0 |
| Herb ext camellia sinensis leaf | 0.002 | 0.0012 | 0.003 | 0.0015 | 0.0015 |
| EUTANOL G | 3.5 | 3.8 | 3.5 | 3.5 | 3.5 |
| CITRIC ACID MONOHYDRATE BP GRAN | 0 | 0 | 0 | 0 | 0 |
| Dimethicone/Dimethiconol | 0 | 0 | 0 | 0 | 0 |
| Ginkgo Biloba leaf extract | 0.0025 | 0.0027 | 0 | 0 | 0 |
| Phytosphingosine | 0.08 | 0 | 0 | 0.08 | 0 |
| Monoammonium glycyrrhizate | 0.5 | 0.5 | 0 | 0 | 0 |
| Shea butter | 0 | 2 | 0 | 0 | 0 |
| Isononyl Isononoate | 0 | 0 | 2 | 0 | 0 |
| Carnauba wax | 0 | 0 | 0 | 3 | 0 |
| Biosaccharide gum | 0 | 0 | 0 | 0 | 5 |

COSMETIC SKINCARE COMPOSITIONS

FIELD OF THE INVENTION

The present invention relates to cosmetic compositions providing improved skin protection and methods of cosmetic treatment using said compositions.

BACKGROUND TO THE INVENTION

The skin is the first line of defence, serving as a barrier between us and the environment. The skin is a complex organ consisting of three layers: the epidermis, dermis and hypodermis.

The epidermis is the outermost layer, which itself is made up of several layers. The outermost portion of the epidermis, known as the stratum corneum, is relatively waterproof and, when undamaged, prevents most bacteria, viruses, and other foreign substances from entering the body. It also prevents the loss of moisture, heat and other important constituents of the body.

Most of the cells (90-95%) in the epidermis are keratinocytes. They originate from proliferating keratinocyte stem cells in the deepest layer of the epidermis called the basal layer. Resulting keratinocytes further divide and differentiate and slowly migrate up toward the surface of the epidermis as mature cells. Once the keratinocytes reach the stratum corneum at the skin surface they are dead and no longer multiplying and are gradually shed and replaced by newer cells pushed up from below.

The skin is subject to constant attack by a variety of both exogenous and endogenous insults. Exogenous insults include those arising from the environment such as ultraviolet radiation (UVA and UVB), infra-red and visible light, atmospheric pollution (including cigarette smoke) and/or harsh chemicals including surfactants in cosmetic formulations. Such environmental factors may either directly or indirectly result in skin damage by the generation of reactive species and free radicals, for example superoxide anions, hydrogen peroxide, hydroxyl ions, peroxyl ions, ozone, singlet oxygen, sulphur oxide, nitrogen oxide, carbon monoxide, alkoxyl ion, peroxynitrite and heavy metals. Reactive oxygen species (ROS), reactive carbonyl species (RCS) and reactive nitrogen species (RNS) need to be particularly considered. Endogenous insults can also result in skin damage, for example hormonal fluctuations (e.g. cortisol and adrenaline hormones), aging and other biochemical changes from within the skin.

With respect to atmospheric pollution (including cigarette smoke), polycyclic aromatic hydrocarbons (PAHs) are key pollutants that cause skin damage through a number of different mechanisms including increased melanocyte activation, increased sebum oxidation and mitochondrial damage of keratinocytes and fibroblasts. PAHs can also increase ROS discussed above in the skin.

The process of keratinocyte cell proliferation, differentiation and maturation is vulnerable to the many exogenous and endogenous insults that the skin faces on a daily basis. These insults are known to increase the inflammatory response in the epidermis. One consequence of this inflammation is the increased proliferation of keratinocytes followed by poor maturation and differentiation thereof, resulting in a lower quality stratum corneum and thus skin barrier disruption and/or damage. Once the skin barrier has been disrupted or damaged this further enhances the cascade of inflammation and keratinocyte over proliferation, creating a cycle of unhealthy skin traits. The skin barrier is weakened to the attack of pathogens and toxins, increasing the likelihood of skin redness and irritation, pimples and spots and/or causing the skin to appear dull, dry and scaly.

SUMMARY OF THE INVENTION

The Applicant has identified a consumer need to provide cosmetic compositions which maintain and/or improve skin health or appearance. The Applicant has surprisingly found that the compositions of the present invention provide superior benefits to the skin in response to exogenous and endogenous insults.

Accordingly, in one aspect of the invention there is provided a cosmetic composition comprising:
(i) a polyphenolic antioxidant agent; and
(ii) a sphingosine compound.

In an alternative aspect of the invention there is provided a cosmetic composition comprising:
(i) a polyphenolic antioxidant agent; and
(ii) a sphingosine compound of Formula (I), or a salt or derivative thereof:

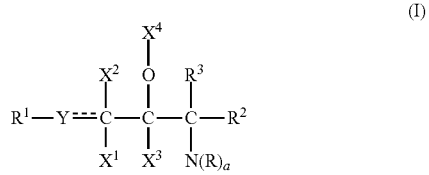

wherein:
$R^1$ is a linear, branched or cyclic, saturated or unsaturated C4-30 hydrocarbon group, which may optionally be substituted by a hydroxyl, carbonyl or amino group, Y is any one of a methylene group ($CH_2$), a methine group (CH) and an oxygen atom, $X^1$, $X^2$ and $X^3$ are each independently a hydrogen atom, a hydroxyl group or an acetoxy group, $X^4$ is a hydrogen atom, an acetyl group, a glyceryl group or a substituent forming an oxo group together with the adjacent oxygen atom.

$R^2$ and $R^3$ are each independently a hydrogen atom, a hydroxyl group, a hydroxymethyl group or an acetoxymethyl group.

a is an integer which is 2 or 3, and each R is each independently a hydrogen atom, or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups, wherein the sphingosine compound is present in an amount about 10 to about 100 times the amount of the polyphenolic antioxidant agent.

Surprisingly, it has been found that by combining a polyphenolic antioxidant agent with a sphingosine compound, improved skin responsiveness to, and/or protection against, exogenous and endogenous insults can be achieved. The agents used in the present invention may already be known to be effective in protecting the skin from exogenous and endogenous insults. However, the efficacy of the combination used in the present invention (especially in the ratio discussed above) is unexpectedly and advantageously greater than the sum of the individual agents. The combination of the agents described by the present invention is therefore "synergistic".

In another aspect of the invention, there is provided a method of cosmetic treatment of a skin condition comprising the step of applying the cosmetic composition according to the invention onto the skin of a subject afflicted with the skin condition or at risk of being afflicted with the skin condition.

In another aspect of the invention, there is provided a use of the cosmetic composition according to the invention as a topical application on the skin.

As previously discussed, it is appreciated that the cosmetic compositions of the present invention can be effective in cosmetically treating skin damage as a result of pollution insult or cosmetically preventing the detrimental effects of pollution insult to the skin. Thus, a further aspect of the present invention provides a method of cosmetically treating skin damage as a result of pollution insult, or of cosmetically preventing the detrimental effects of pollution to the skin, said method comprising applying an effective amount of cosmetic composition defined above to the skin.

DETAILED DESCRIPTION OF THE INVENTION

The invention makes use of a polyphenolic antioxidant agent. The term "polyphenolic" can be defined as a compound which possesses aromatic rings bearing one or more hydroxy substituents, including functional derivatives.

The term "polyphenolic antioxidant agent" is intended to mean a plant, algal or fungal extract, or derivative thereof, comprising one or more species which provide an antioxidant benefit, such as *flavonoid* species; phenolic acid species; stilbene species; lignin species, or combinations thereof.

In one embodiment the polyphenolic antioxidant agent comprises one or more *flavonoid* species. *Flavonoid* species include flavones, flavonols, flavanones, flavanols, anthocyanidins, anthocyanins, proanthocyanidins, flavans, isoflavones and isoflavonoids. Some specific examples of *flavonoid* species are catechins (catechin, epicatechin, gallocatechin, epigallocatechin, epicatechin gallate, epigallocatechin gallate), quercetin, rutin, hesperidin and genistein.

Plants provide a rich and cheap source of polyphenolic antioxidant agents, and are therefore an efficient source of said agents. Naturally occurring polyphenolic antioxidant agents may therefore be used.

However, the same or similar actives can be also prepared synthetically. The term "polyphenolic antioxidant agent" is therefore intended to cover synthetic polyphenols, such as synthetic analogues of naturally occurring polyphenolic antioxidant agents. Thus chemically synthesized or purified polyphenols and mixtures thereof may be used in place of plant extracts. Polyphenols may be synthesized or extracted from natural sources by any suitable method known to those skilled in the art, particularly using food-grade solvents. Liquid and solid (e.g. granulate or powder form) extracts are suitable.

Extracts (e.g. aqueous or alcoholic) can be obtained from plant parts including but not limited to leaves, raw or cooked whole fruit, berries and vegetables, nuts, the skins of fruit, fruit flesh, fruit rind, peel, pips, cones (e.g. hops), seeds or stones, bark, buds, flowers or parts thereof, including petals and pollen, roots, rhizomes and tubers, and stems. The plant extract may be selected from the group consisting of essential oils, extracts from leaves, extracts from stems, extracts from petals, extracts from seeds, extracts from roots, extracts from pollen, and combinations thereof. In one embodiment, extracts (e.g. lyophilised extracts) from leaves are used.

The polyphenolic antioxidant agent may be selected from the group consisting of extracts of: green tea (e.g. green leaves of *Camellia sinensis*), mulberry (e.g. *Morus alba*), ginseng (e.g. *Panex ginseng*), raspberry, oregano (e.g. *Origanum vulgare*), white tea (e.g. *Camellia sinensis*), red tea, Mohani tea, black tea, Oolong tea, yellow tea, jasmine tea, Pu Erh tea, blueberry (e.g. *Vaccinium cyanococcus*), French maritime pine bark (e.g. *Pinus pinaster*, sold under the tradename of Pycnogenol), rosemary (e.g. *Rosmarinus officialis*), grape, including grape seed (e.g. *Vitis vinifera*), fennel (e.g. *Foeniculi fructus*), *Caragana sinica*, majaoram (e.g. *Origanum majorana*), crocus (e.g. *Crocus sativus*), apple (e.g. *Malus domestica*), coffee, green coffee, cherry (e.g. *Prunus avium*), snow algae (e.g. *Chlamydomonas nivalis*), Emblica (e.g. *Pyllanthus emblica*), ginkgo (e.g. *Ginkgo biloba*), moringa (e.g. *Moringa oleilera*), ginger, magnolia (e.g. *Magnolioideae virginiana*), French saffron, edelweiss (e.g. *Leontopodium alpinium*), white lotus (e.g. *Nymphaea alba*), turmeric root, marshmallow (e.g. *Althaea officianlis*), burdock (e.g. *Arctium lappa*), bilberry (e.g. *Vaccinium myrtillus*), cranberry (e.g. *Vaccinium oxycoccus*), pomegranate (e.g. *Punica granatum*), sage (e.g. *Salvia officianlis*), thyme (e.g. *Thymus vulgaris*), sunflower (e.g. *Helianthus annus*), wild carrot (e.g. *Daucus carota*), hop (e.g. *Humulus lupulus*), witch hazel (e.g. *Hamamelis*), oak (e.g. *Quercus*), Camellia (e.g. *Theacea*), red clover (e.g. *Tritolium pratense*), flax (e.g. *Linium usitatissiumum*), lemon (e.g. *Citrus limon*), birch (e.g. *Betula*), cornflower (e.g. *Centaurea cyanus*), geranium, polygonum, soy (e.g. *Glycine max*), Sophora (e.g. *Sophora flavescens*), and combinations thereof.

In one embodiment, the polyphenolic antioxidant agent is selected from the group consisting of extracts of: green tea (e.g. green leaves of *C. sinensis*), white tea (e.g. *C. sinensis*), red tea, Mohani tea, black tea, Oolong tea, yellow tea, jasmine tea, Pu Erh tea, mulberry (e.g. *M. alba*), ginseng (e.g. *P. ginseng*), rosemary (e.g. *R. officialis*), blueberry (e.g. *V. cyanococcus*), apple (e.g. *M. domestica*), cherry (e.g. *P. avium*), Emblica (e.g. *P. emblica*), ginkgo (e.g. *G. biloba*), moringa (e.g. *M. oleilera*), white lotus (e.g. *N. alba*), marshmallow (e.g. *A. officianlis*), bilberry (e.g. *V. myrtillus*), cranberry (e.g. *V. oxycoccus*), pomegranate (e.g. *P. granatum*), thyme (e.g. *T. vulgaris*), cornflower (e.g. *C. cyanus*), geranium, polygonum, soy (e.g. *G. max*), Sophora (e.g. *S. flavescens*), burdock (e.g. *A. lappa*) and combinations thereof.

In one embodiment, the polyphenolic antioxidant agent is selected from the group consisting of extracts of: green tea (e.g. *C. sinensis*), ginkgo (e.g. *G. biloba*), Emblica (e.g. *P. emblica*), mulberry (e.g. *M. alba*), ginseng (e.g. *P. ginseng*), Sophora (e.g. *S. flavescens*), and combinations thereof.

In one embodiment, the polyphenolic antioxidant agent comprises extracts of green tea. In addition, the cosmetic composition may optionally further comprise extracts of white tea, blueberry, apple, cherry, Emblica, ginkgo, moringa, white lotus, marshmallow, bilberry, cranberry, pomegranate, thyme, cornflower, geranium, polygonum, soy or combinations thereof.

In one embodiment the polyphenolic antioxidant agent has a polyphenol content of 50% or more by dry weight, e.g. 60% or more or 65% or more or 70% or more or 75% or more by dry weight.

The polyphenolic antioxidant agent may be present in an amount of about 0.0001% to about 20% by weight of the composition, about 0.0001% to about 15% by weight of the composition, about 0.0001% to about 10% by weight of the composition, about 0.0001% to about 5% by weight of the composition, about 0.0005 to about 5% by weight of the composition. In one embodiment, the polyphenolic antioxidant agent is present in an amount of about 0.0001% to about 5% by weight of the composition.

The invention also makes use of a sphingosine compound. In one aspect of the present invention, the sphingosine compound is a compound of Formula (I), or a salt or derivative thereof:

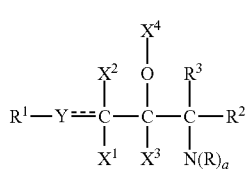
(I)

wherein:
- $R^1$ is a linear, branched or cyclic, saturated or unsaturated C4-30 hydrocarbon group, which may optionally be substituted by a hydroxyl, carbonyl or amino group,
- Y is any one of a methylene group ($CH_2$), a methine group (CH) and an oxygen atom,
- $X^1$, $X^2$ and $X^3$ are each independently a hydrogen atom, a hydroxyl group or an acetoxy group,
- $X^4$ is a hydrogen atom, an acetyl group, a glyceryl group or a substituent forming an oxo group together with the adjacent oxygen atom.
- $R^2$ and $R^3$ are each independently a hydrogen atom, a hydroxyl group, a hydroxymethyl group or an acetoxymethyl group.
- a is an integer which is 2 or 3, and
- each R is each independently a hydrogen atom, or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups.

The derivative may be an N-acyl, O-acyl or N-alkyl derivative. In one embodiment it is an N-acyl or N-alkyl derivative.

The salt may, for example, be a hydrochloride, phosphate, sulphate, nitrate, chloride, or other soluble salt.

In one embodiment $R^1$ is a linear, branched or cyclic, saturated or unsaturated C7-22 (e.g. C8-C20 or C9-C20) hydrocarbon group which may be substituted by a hydroxyl group. In one embodiment $R^1$ is a linear or branched C10-20 (e.g. C12-C18) alkyl group, or a linear or branched C10-20 (e.g. C12-C18) alkyl group having, at a terminal thereof on the Y side, a hydroxyl group. When it is a branched alkyl group, it preferably is a methyl-branched alkyl chain. Examples include tridecyl, tetradecyl, pentadecyl, hexadecyl, 1-hydroxytridecyl, 1-hydroxypentadecyl, isohexadecyl and isostearyl groups.

In one embodiment, at most one (i.e. none or exactly one) of the $X^1$, $X^2$ and $X^3$ groups is a hydroxyl group, the remainder of the $X^1$, $X^2$ and $X^3$ groups are each a hydrogen atom, and $X^4$ is a hydrogen atom.

When Y is a methine group, either $X^1$ or $X^2$ is a hydrogen atom and the other one does not exist.

When $X^4$ forms an oxo group, $X^3$ does not exist.

In one embodiment, one of $R^2$ and $R^3$ is a hydrogen atom. In one embodiment, one of $R^2$ and $R^3$ is a hydroxymethyl group. In one embodiment, one of $R^2$ and $R^3$ is a hydrogen atom and the other is a hydroxymethyl group.

As noted above, the R groups may be an optionally substituted hydrocarbon group. In one embodiment, the hydroxyalkoxy group which may be a substituent for the hydrocarbon group is a linear or branched C1-7 hydroxyalkoxy group and the alkoxy group which may be a substituent for the hydrocarbon group is a linear or branched C1-7 alkoxy group.

In one embodiment, the R groups are independently selected from a hydrogen atom; linear or branched alkyl groups such as methyl, ethyl, propyl, 2-ethylhexyl and isopropyl; alkenyl groups such as vinyl and allyl; amidino groups; and hydrocarbon groups having 1 to 8 carbon atoms in total and having 1 to 6 substituents selected from hydroxyl group, hydroxyalkoxy group and alkoxy groups, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl.

In one embodiment, the R groups are independently selected from a hydrogen atom, a methyl group, and an alkyl group which may be substituted by 1 to 3 substituents selected from hydroxyl group and hydroxyalkoxy groups, such as 2-hydroxyethyl, 1,1-dimethyl-2-hydroxyethyl, 1,1-bis(hydroxymethyl)ethyl, 2-(2-hydroxyethoxy)ethyl.

In one embodiment, the R groups are each hydrogen.

The sphingosine compound may be selected from the group consisting of: sphingosine; phytosphingosine; dihydrosphingosine; derivatives thereof (including salts thereof); and combinations thereof. For example, the sphingosine compound may be an N-acyl, O-acyl or N-alkyl derivative. The sphingosine compound may be a salt, for example phytosphingosine hydrochloride.

The sphingosine compound may be a ceramide, for example ceramide 1, ceramide 2, ceramide 3 and/or ceramide 6. However, in another embodiment, the sphingosine compound is not a ceramide.

For the sphingosine compound, the natural (D(+) form) optically active derivatives, the natural (L(−) form) optically active derivatives, or a mixture thereof, may be used. The relative configuration of the sphingosine compounds may therefore be any one of the natural form, an unnatural form, or a mixture thereof.

In one embodiment, the sphingosine compound is selected from the group consisting of:

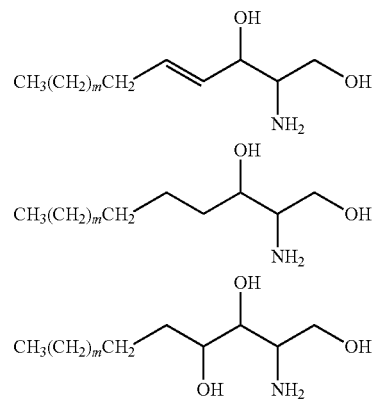

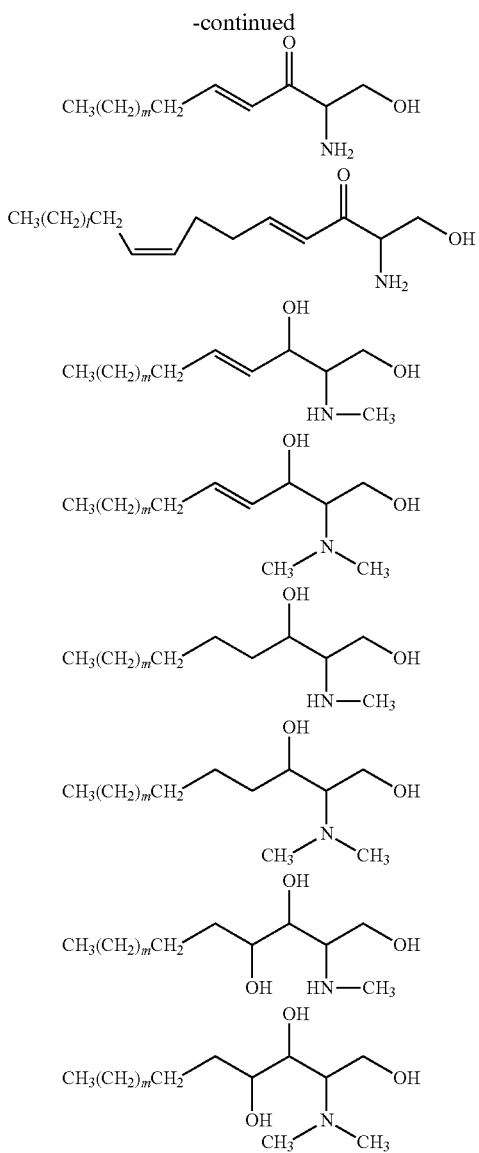

wherein m is an integer from 5 to 17 and 1 is an integer from 1 to 13.

In one embodiment, the sphingosine compound is selected from the group consisting of: natural sphingosine, dihydrosphingosine (sphinganine), phytosphingosine, sphingadienine, dehydrosphingosine, and dehydrophytosphingosine, salts thereof (e.g. phytosphingosine hydrochloride), and N-alkyl derivatives (e.g., N-methyl derivatives) thereof.

In one embodiment, the sphingosine compound is selected from the group consisting of dihydrosphingosine (sphinganine), phytosphingosine, salicyloyl phytosphingosine (phytosphingosine SLC), phytosphingosine hydrochloride (phytosphingosine HCl), sphingonine hydroxysphingosine, and sphingosine-1-phosphate, and combinations thereof.

In one embodiment, the sphingosine compound comprises phytosphingosine hydrochloride.

The sphingosine compound may be natural or may be synthetic. Thus it may be obtained from any suitable source, for example from a natural source or from a chemical synthesis process. The sphingosine compound may be obtained from an animal source, a plant source, a yeast source, or combinations thereof. In one embodiment, the sphingosine compound is obtained from a plant source.

The sphingosine compound may be present in an amount of from about 0.001% to about 20% by weight of the composition, e.g. from about 0.01% to about 20% by weight of the composition, about 0.01% to about 10% by weight of the composition, about 0.01% to about 5% by weight of the composition, or about 0.01 to about 3% by weight of the composition. In one embodiment, the sphingosine compound is present in an amount of from about 0.01% to about 1% by weight of the composition.

The cosmetic composition of the invention may comprise the sphingosine compound in at least the same amount of or more than the amount of the polyphenolic antioxidant agent. For example, the cosmetic composition of the invention may comprise the sphingosine compound in an amount about 100 times or less the amount of the polyphenolic antioxidant agent. For example, about 95 times or less, about 90 times or less, about 85 times or less, about 80 times or less, about 75 times or less, about 70 times or less, about 65 times or less, about 60 times or less, about 55 times or less, about 50 times or less, about 45 times or less, about 40 times or less, about 35 times or less, about 30 times or less, about 25 times or less, about 20 times or less, about 15 times or less, about 10 times or less, about 5 times or less, about 3 times or less, or about 2 times or less.

The total amount of the polyphenolic antioxidant agent and the sphingosine compound in the cosmetic composition of the invention may be an amount of from about 0.0001% to about 20% by weight of the composition, e.g. 0.0001% to about 10%, 0.0001% to about 5%, about 0.0001% to about 2%, about 0.0001% to about 1%, about 0.0001% to about 1% or about 0.001% to about 0.1% by weight of the composition. In one embodiment, the cosmetic composition of the invention comprises the polyphenolic antioxidant agent and the sphingosine compound in an amount of from about 0.005% to about 0.1% by weight of the composition.

The cosmetic composition of the invention may comprise the polyphenolic antioxidant agent in an amount of from about 0.0001% to about 10% by weight of the composition, e.g. from about 0.0001% to about 5%, about 0.0001% to about 2%, about 0.0001% to about 1%, about 0.0005% to about 1%, about 0.0005% to about 0.5%, or about 0.001% to about 1% by weight of the composition and the sphingosine compound in an amount of from about 0.001% to about 5%, e.g. about 0.001% to about 2%, about 0.005% to about 2%, about 0.01% to about 2%, about 0.01% to about 1%, or about 0.01% to about 0.5% by weight of the composition. In one embodiment, the cosmetic composition of the invention comprises the polyphenolic antioxidant agent in an amount of from about 0.001% to about 5% (e.g. about 0.0001% to about 2%, about 0.001% to about 1%) by weight of the composition and the sphingosine compound in an amount of about 0.01% to about 5% (e.g. about 0.01% to about 2%, about 0.01% to about 1%) by weight of the composition.

The cosmetic composition of the invention may comprise the polyphenolic antioxidant agent and the sphingosine compound in an amount effective to inhibit interleukin-6 (IL-6) by at least about 80%, by at least about 75%, by at least about 70%, by at least about 60%, by at least about 50%, by at least about 40%, by at least about 30%, or by at least about 25%. In one embodiment, the cosmetic composition of the invention may comprise the polyphenolic antioxidant agent and the sphingosine compound in an amount effective to inhibit interleukin-6 (IL-6) by at least about 50%. A suitable technique for measuring IL-6 inhibition is described in detail in the Examples section of the specification.

Surprisingly, the effect of using the polyphenolic antioxidant agent and the sphingosine compound in combination gives rise to a more than additive effect in terms of inhibiting interleukin-6 (IL-6) (especially when the sphingosine compound is present in an amount about 10 to about 100 times the amount of the polyphenolic antioxidant agent). Therefore there is a technical benefit to using the two agents in a single formulation that would not have been foreseen. For example, when green tea and phytosphingosine hydrochloride are used in combination in the cosmetic composition, according to the invention, the percentage of interleukin-6 (IL-6) inhibition is about 50%. Furthermore, increases in IL-6 inhibition are seen when phytosphingosine hydrochloride and green tea are used in combination at ratios of 1:10, 1:50 and 1:100 compared to phytosphingosine hydrochloride or green tea alone. These results show more than the additive effect (in terms of inhibiting interleukin-6) of the two ingredients individually.

In one aspect, the cosmetic composition of the invention comprises:
(i) a polyphenolic antioxidant agent selected from the group consisting of extracts of: green tea (e.g. green leaves of $C.$ $sinensis$), mulberry (e.g. $M.$ $alba$), ginseng (e.g. $P.$ $ginseng$), raspberry, oregano (e.g. $O.$ $vulgare$), white tea (e.g. $C.$ $sinensis$), red tea, Mohani tea, black tea, Oolong tea, yellow tea, jasmine tea, Pu Erh tea, blueberry (e.g. $V.$ $cyanococcus$), French maritime pine bark (e.g. $P.$ $pinaster$, sold under the tradename of Pycnogenol), rosemary (e.g. $R.$ $officialis$), grape, including grape seed (e.g. $V.$ $vinifera$), fennel (e.g. $F.$ $fructus$), $C.$ $sinica$, majaoram (e.g. $O.$ $majorana$), crocus (e.g. $C.$ $sativus$), apple (e.g. $M.$ $domestica$), coffee, green coffee, cherry (e.g. $P.$ $avium$), snow algae (e.g. $C.$ $nivalis$), $Emblica$ (e.g. $P.$ $emblica$), ginkgo (e.g. $G.$ $biloba$), moringa (e.g. $M.$ $oleilera$), ginger, magnolia (e.g. $M.$ $virginiana$), French saffron, edelweiss (e.g. $L.$ $alpinium$), white lotus (e.g. $N.$ $alba$), turmeric root, marshmallow (e.g. $A.$ $officianlis$), burdock (e.g. $A.$ $lappa$), bilberry (e.g. $V.$ $myrtillus$), cranberry (e.g. $V.$ $oxycoccus$), pomegranate (e.g. $P.$ $granatum$), sage (e.g. $S.$ $officianlis$), thyme (e.g. $T.$ $vulgaris$), sunflower (e.g. $H.$ $annus$), wild carrot (e.g. $D.$ $carota$), hop (e.g. $H.$ $lupulus$), witch hazel (e.g. $Hamamelis$), oak (e.g. $Quercus$), $Camellia$ (e.g. $Theacea$), red clover (e.g. $T.$ $pratense$), flax (e.g. $L.$ $usitatissiumum$), lemon (e.g. $C.$ $limon$), birch (e.g. $Betula$), cornflower (e.g. $C.$ $cyanus$), geranium, polygonum, soy (e.g. $G.$ $max$), $Sophora$ (e.g. $S.$ $flavescens$), and combinations thereof; and
(ii) a sphingosine compound.

In an alternative aspect of the invention there is provided a cosmetic composition comprising:
(i) a polyphenolic antioxidant agent selected from the group consisting of extracts of: green tea (e.g. green leaves of $C.$ $sinensis$), mulberry (e.g. $M.$ $alba$), ginseng (e.g. $P.$ $ginseng$), raspberry, oregano (e.g. $O.$ $vulgare$), white tea (e.g. $C.$ $sinensis$), red tea, Mohani tea, black tea, Oolong tea, yellow tea, jasmine tea, Pu Erh tea, blueberry (e.g. $V.$ $cyanococcus$), French maritime pine bark (e.g. $P.$ $pinaster$, sold under the tradename of Pycnogenol), rosemary (e.g. $R.$ $officialis$), grape, including grape seed (e.g. $V.$ $vinifera$), fennel (e.g. $F.$ $fructus$), $C.$ $sinica$, majaoram (e.g. $O.$ $majorana$), crocus (e.g. $C.$ $sativus$), apple (e.g. $M.$ $domestica$), coffee, green coffee, cherry (e.g. $P.$ $avium$), snow algae (e.g. $C.$ $nivalis$), $Emblica$ (e.g. $P.$ $emblica$), ginkgo (e.g. $G.$ $biloba$), moringa (e.g. $M.$ $oleilera$), ginger, magnolia (e.g. $M.$ $virginiana$), French saffron, edelweiss (e.g. $L.$ $alpinium$), white lotus (e.g. $N.$ $alba$), turmeric root, marshmallow (e.g. $A.$ $officianlis$), burdock (e.g. $A.$ $lappa$), bilberry (e.g. $V.$ $myrtillus$), cranberry (e.g. $V.$ $oxycoccus$), pomegranate (e.g. $P.$ $granatum$), sage (e.g. $S.$ $officianlis$), thyme (e.g. $T.$ $vulgaris$), sunflower (e.g. $H.$ $annus$), wild carrot (e.g. $D.$ $carota$), hop (e.g. $H.$ $lupulus$), witch hazel (e.g. $Hamamelis$), oak (e.g. $Quercus$), $Camellia$ (e.g. $Theacea$), red clover (e.g. $T.$ $pratense$), flax (e.g. $L.$ $usitatissiumum$), lemon (e.g. $C.$ $limon$), birch (e.g. $Betula$), cornflower (e.g. $C.$ $cyanus$), geranium, polygonum, soy (e.g. $G.$ $max$), $Sophora$ (e.g. $S.$ $flavescens$), and combinations thereof; and
(ii) a sphingosine compound of Formula (I), or a salt or derivative thereof:

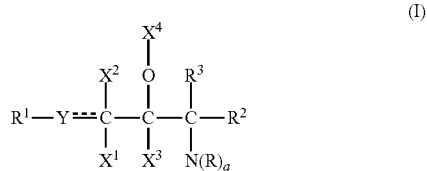

wherein:
$R^1$ is a linear, branched or cyclic, saturated or unsaturated C4-30 hydrocarbon group, which may optionally be substituted by a hydroxyl, carbonyl or amino group,
Y is any one of a methylene group ($CH_2$), a methine group (CH) and an oxygen atom,
$X^1$, $X^2$ and $X^3$ are each independently a hydrogen atom, a hydroxyl group or an acetoxy group,
$X^4$ is a hydrogen atom, an acetyl group, a glyceryl group or a substituent forming an oxo group together with the adjacent oxygen atom.
$R^2$ and $R^3$ are each independently a hydrogen atom, a hydroxyl group, a hydroxymethyl group or an acetoxymethyl group.
a is an integer which is 2 or 3, and
each R is each independently a hydrogen atom, or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups,
wherein the sphingosine compound is present in an amount about 10 to about 100 times the amount of the polyphenolic antioxidant agent.

In one embodiment (and in some of the alternative aspects presented above), the cosmetic composition of the invention may comprise the sphingosine compound in an amount of from about 10 to about 100 times the amount of the polyphenolic antioxidant agent. Preferably the cosmetic composition comprises the sphingosine compound in an amount of from about 25 times to about 75 times or from about 40 times to about 80 times the amount of the polyphenolic antioxidant agent.

In one embodiment, the cosmetic composition of the invention comprises:
(i) a polyphenolic antioxidant agent; and
(ii) a sphingosine compound selected from the group consisting of dihydrosphingosine (sphinganine), phytosphingosine, salicyloyl phytosphingosine (phytosphingosine SLC), phytosphingosine hydrochloride (phytosphingosine HCl), sphingonine hydroxysphingosine, and sphingosine-1-phosphate, and combinations thereof. In one such embodiment, the cosmetic composition of the invention may comprise the sphingosine compound in an amount of from about 10 to about 100 times (e.g. about 25 times to about 75 times, about 40 times to about 80 times) the amount of the polyphenolic antioxidant agent.

In one embodiment, the cosmetic composition of the invention comprises:
(i) a polyphenolic antioxidant agent selected from the group consisting of extracts of: green tea (e.g. green leaves of *C. sinensis*), mulberry (e.g. *M. alba*), ginseng (e.g. *P. ginseng*), raspberry, oregano (e.g. *O. vulgare*), white tea (e.g. *C. sinensis*), red tea, Mohani tea, black tea, Oolong tea, yellow tea, jasmine tea, Pu Erh tea, blueberry (e.g. *V. cyanococcus*), French maritime pine bark (e.g. *P. pinaster*, sold under the tradename of Pycnogenol), rosemary (e.g. *R. officialis*), grape, including grape seed (e.g. *V. vinifera*), fennel (e.g. *F. fructus*), *C. sinica*, majaoram (e.g. *O. majorana*), crocus (e.g. *C. sativus*), apple (e.g. *M. domestica*), coffee, green coffee, cherry (e.g. *P. avium*), snow algae (e.g. *C. nivalis*), Emblica (e.g. *P. emblica*), ginkgo (e.g. *G. biloba*), moringa (e.g. *M. oleilera*), ginger, magnolia (e.g. *M. virginiana*), French saffron, edelweiss (e.g. *L. alpinium*), white lotus (e.g. *N. alba*), turmeric root, marshmallow (e.g. *A. officianlis*), burdock (e.g. *A. lappa*), bilberry (e.g. *V. myrtillus*), cranberry (e.g. *V. oxycoccus*), pomegranate (e.g. *P. granatum*), sage (e.g. *S. officianlis*), thyme (e.g. *T. vulgaris*), sunflower (e.g. *H. annus*), wild carrot (e.g. *D. carota*), hop (e.g. *H. lupulus*), witch hazel (e.g. *Hamamelis*), oak (e.g. *Quercus*), Camellia (e.g. *Theacea*), red clover (e.g. *T. pratense*), flax (e.g. *L. usitatissiumum*), lemon (e.g. *C. limon*), birch (e.g. *Betula*), cornflower (e.g. *C. cyanus*), geranium, polygonum, soy (e.g. *G. max*), Sophora (e.g. *S. flavescens*), and combinations thereof; and
(ii) a sphingosine compound selected from the group consisting of dihydrosphingosine (sphinganine), phytosphingosine, salicyloyl phytosphingosine (phytosphingosine SLC), phytosphingosine hydrochloride (phytosphingosine HCl), sphingonine hydroxysphingosine, and sphingosine-1-phosphate, and combinations thereof. In one such embodiment, the cosmetic composition of the invention may comprise the sphingosine compound in an amount of from about 10 to about 100 times (e.g. about 25 times to about 75 times, about 40 times to about 80 times) the amount of the polyphenolic antioxidant agent.

In one embodiment, the cosmetic composition of the invention comprises:
(i) a polyphenolic antioxidant agent selected from the group consisting of extracts of: green tea (e.g. *C. sinensis*), ginkgo (e.g. *G. biloba*), Emblica (e.g. *P. emblica*), mulberry (e.g. *M. alba*), ginseng (e.g. *P. ginseng*), Sophora (e.g. *S. flavescens*), and combinations thereof; and
(ii) a sphingosine compound selected from the group consisting of dihydrosphingosine (sphinganine), phytosphingosine, salicyloyl phytosphingosine (phytosphingosine SLC), phytosphingosine hydrochloride (phytosphingosine HCl), sphingonine hydroxysphingosine, and sphingosine-1-phosphate, and combinations thereof, (e.g. phytosphingosine hydrochloride, phytosphingosine, sphinganine, and combinations thereof). In one such embodiment, the cosmetic composition of the invention may comprise the sphingosine compound in an amount of from about 10 to about 100 times (e.g. about 25 times to about 75 times, about 40 times to about 80 times) the amount of the polyphenolic antioxidant agent.

In one embodiment, the cosmetic composition of the invention comprises: (i) a polyphenolic antioxidant agent comprising an extract of green tea; and (ii) a sphingosine compound. In one such embodiment, the cosmetic composition of the invention may comprise the sphingosine compound in an amount of from about 10 to about 100 times (e.g. about 25 times to about 75 times, about 40 times to about 80 times) the amount of the polyphenolic antioxidant agent.

In one embodiment, the cosmetic composition of the invention comprises: (i) a polyphenolic antioxidant agent comprising an extract of green tea; and (ii) a sphingosine compound selected from the group consisting of phytosphingosine hydrochloride, phytosphingosine, sphinganine, and combinations thereof. In one such embodiment, the cosmetic composition of the invention may comprise the sphingosine compound in an amount of from about 10 to about 100 times (e.g. about 25 times to about 75 times, about 40 times to about 80 times) the amount of the polyphenolic antioxidant agent.

In one embodiment, the cosmetic composition of the invention comprises:
(i) from about 0.0001% to about 5% by weight of the composition of a polyphenolic antioxidant agent selected from the group consisting of extracts of: green tea (e.g. green leaves of *C. sinensis*), white tea (e.g. *C. sinensis*), red tea, Mohani tea, black tea, Oolong tea, yellow tea, jasmine tea, Pu Erh tea, mulberry (e.g. *M. alba*), ginseng (e.g. *P. ginseng*), rosemary (e.g. *R. officialis*), blueberry (e.g. *V. cyanococcus*), apple (e.g. *M. domestica*), cherry (e.g. *P. avium*), Emblica (e.g. *P. emblica*), ginkgo (e.g. *G. biloba*), moringa (e.g. *M. oleilera*), white lotus (e.g. *N. alba*), marshmallow (e.g. *A. officianlis*), bilberry (e.g. *V. myrtillus*), cranberry (e.g. *V. oxycoccus*), pomegranate (e.g. *P. granatum*), thyme (e.g. *T. vulgaris*), cornflower (e.g. *C. cyanus*), geranium, polygonum, soy (e.g. *G. max*), Sophora (e.g. *S. flavescens*), burdock (e.g. *A. lappa*) and combinations thereof; and
(ii) about 0.01% to about 5% of a sphingosine compound selected from the group consisting of dihydrosphingosine (sphinganine), phytosphingosine, salicyloyl phytosphingosine (phytosphingosine SLC), phytosphingosine hydrochloride (phytosphingosine HCl), sphingonine hydroxysphingosine, and sphingosine-1-phosphate, and combinations thereof, (e.g. phytosphingosine hydrochloride, phytosphingosine, sphinganine, and combinations thereof).

In one such embodiment, the cosmetic composition of the invention may comprise the sphingosine compound in an amount of from about 10 to about 100 times (e.g. about 25 times to about 75 times, about 40 times to about 80 times) the amount of the polyphenolic antioxidant agent.

The cosmetic composition of the invention may comprise a cosmetically acceptable carrier.

The cosmetically acceptable carrier may be water-based, oil-or wax-based, or emulsion-based.

In embodiments where the carrier is emulsion-based, the composition may be in the form of a water-in-oil, an oil-in-water, a water-in-oil-in-water or an oil-in-water-in-oil emulsion.

In embodiments where the carrier is water-based, water may be present at a level of about 40% or more, about 45% or more, about 50% or more, about 55% or more, or about 60% or more by weight of the composition.

In embodiments where the carrier is oil-or wax-based, the oil and/or wax may be present at a level of about 15% or more, about 20% or more, about 30% or more, about 25% or more, about 35% or more, or about 40% or more by weight of the composition.

For example, in one embodiment the carrier may be water based and may comprise de-ionized water, purified water, natural spring water, rose water or the like. Mixtures of more than one of these may also be used. In one embodiment de-ionized or purified water is used.

The water based carrier may be 100% water or it may comprise components other than water. These may be components known for use in cosmetic formulations. They may include, but are not limited to, agents such as water-soluble moisturising agents, conditioning agents, anti-microbials, humectants (e.g. glycerin) and/or other water-soluble skin care actives.

In another embodiment, the carrier may be oil or wax based. The oil may be natural oil or synthetic oil, but preferably is natural oil such as a vegetable oil or a nut oil. The oil may be liquid or solid. The wax is preferably a natural wax.

Clearly the oil or wax that is chosen must be able to act as a carrier. Preferably it is a material that can easily be blended at room temperature; thus it may be a liquid at room temperature or a solid that is stirrable at room temperature.

Combinations of one or more oils and/or one or more waxes may be used.

Liquid oils that can be mentioned include avocado oil, *Camellia* oil, turtle bean oil, macadamia nut oil, corn oil, mink oil, olive oil, Canoga oil, egg yolk oil, sesame seed oil, Persic oil, wheatgerm oil, *Camellia sasanqua* oil, castor oil, linseed oil, safflower oil, sunflower oil, grapeseed oil, apricot oil, shea oil, sweet almond oil, cotton oil, evening primrose oil, palm oil, perilla oil, hazelnut oil, soybean oil, peanut oil, tea seed oil, kaya oil, rice bran oil, rapeseed oil, alfalfa oil, Chinese tung tree wood oil, Japanese tung tree wood oil, jojoba oil, germ oil, poppyseed oil, pumpkin oil, blackcurrant oil, millet oil, barley oil, quinoa oil, rye oil, candlenut oil, passionflower oil, musk rose oil, triglycerine, glyceryl trioctanoate, and glyceryl triisopalmitate.

Solid oils/fats that can be mentioned include cocoa butter, coconut butter, horse fat, hardened coconut oil, palm oil, beef tallow, mutton tallow, hardened beef tallow, palm kernel oil, lard, Japan wax kernel oil, hardened oil, Japan wax, shea butter, and hardened castor oil.

Waxes that can be mentioned include beeswax, candelilla wax, carnauba wax, lanolin, lanolin acetate, liquid lanolin, sugar cane wax, fatty acid isopropyl lanolin, hexyl laurate, reduced lanolin, jojoba wax, hard lanolin, polyoxyethylene (hereinafter referred to as POE), lanolin alcohol ether, POE lanolin alcohol acetate, lanolin fatty acid polyethylene glycol, and POE hydrogenated lanolin alcohol ether. In one embodiment the carrier is not lanolin based.

Ester oils that can be mentioned include C12-C15 alcohols benzoate, tridecyl salicylate, dibutyl adipate, isopropyl myristate, cetyl octoate, octyldodecil myristate, isopropyl palmitate, butyl stearate, hexyl laurate, myristyl myristate, decyloleate, hexyldecyl dimethyl octoate, cetyl lactate, myristyl lactate, lanolin acetate, isocetyl stearate, isocetyl iso-stearate, 12-hydroxy cholesteryl stearate, di-2-ethylhexylic acid ethyleneglycol, dipentaerythritol fatty acid ester, N-alkylglycol monoisostearate, neopentylglycol dicaprate, diisostearyl malate, glyceryl di-2-heptyl undecanate, tri-methylol propane tri-2-ethylhexyl acid, tri-methylol propane triisostearate, pentaerythritol tetra-2-ethylhexyl acid, glyceryl tri-2-ethyl-hexanoate, tri-methylol propane triisostearate, cetyl-2-ethylexanoate, 2-ethylhexyl-palmitate, glycerine trimyristate, glyceride tri-2-heptyl undecatoic acid, methyl ester of castor oil fatty acid, oleate oil, acetoglyceride, palmitate-2-heptyl undecyl, diisopropyl adipate, N-lauroyl-L-glutamic acid-2-octyldodecil ester, di-2-heptylundecyl adipate, di-2-ethylhexyl sebacate, myristate-2-hexyldecyl, palmitate-2-hexyldecyl, adipate-2-hexyldecyl, diisopropyl sebacate, and succinate-2-ethylhexyl.

Higher fatty acids that can be mentioned include lauric acid, myristic acid, palmitic acid, stearic acid, behenic acid, oleic acid, 12-hydroxy-stearic acid, undecylenic acid, lanolin fatty acid, isostearic acid, linoleic acid, linolenic acid, and eicosapentaenoic acid.

Higher alcohols of straight/branched chain that can be mentioned include lauryl alcohol, cetyl alcohol, stearyl alcohol, behenyl alcohol, myristyl alcohol, oleyl alcohol, cetostearyl alcohol, monostearyl glycerine ether (batyl alcohol), 2-decyltetradecinol, lanolin alcohol, cholesterol, phytosterol, hexyldodecanol, isostearyl alcohol, octyldodecanol.

The cosmetic composition of the invention may be provided in any form suitable for topical application to the skin. The cosmetic composition of the invention may be delivered and/or applied to the skin via any of the conventional formulations known to those skilled in the art. Typical formulation types of the present invention are creams, lotions, milks, gels, serum, foams, and ointments. In one embodiment, the cosmetic composition of the present invention is in the form of a cream or lotion.

The cosmetic composition of the invention will generally further comprise other ingredients or excipients which will be well known to those skilled in the art.

The cosmetic composition of the invention may further comprise one or more humectants, including but not limited to glycerin, propylene glycol, propanediol, butylene glycol, pentylene glycol, hexylene glycol, hexanediol, dipropylene glycol, polyethylene glycol, sorbitol, sodium hyaluronate, urea, xylitol, lactitol, fructose, glucose, mannose, xylose, honey, pyrrolidone, and carboxylic acid and salts thereof. When present, the one or more humectants may be present in the cosmetic composition in an amount of from about 0.01% to about 20% by weight of the composition, e.g. from about 0.1% to about 10%, or about 0.5% to about 7% by weight of the composition.

The cosmetic composition of the invention may further comprise one or more emollients, including but not limited to PPG-15 stearyl ether, ethylhexyl stearate, cetyl dimethicone, octyldodecanol, PPG-20 methyl glucose ether, isopropyl myristate, isopropyl paltimate, isopropyl laurate, isodecyl laurate, isodecyl neopentanoate, isohexadecane, pentaerythrityl tetraisostearate, caprylic/capric triglyceride, canola oil, sunflower oil (*H. annus*), olive oil (*Olea europea*), cottonseed oil (*Gossypium herbaceum*), jojoba oil (*Simmondsia chinensis*), shea butter (*Butyrospermum parkii*), cocoa butter (*Theobroma cacao*), cupuacu butter (*Theobroma grandiflorum*), avocado oil (*Persea gratissima*), liquid paraffin, dimethicone, phenyl trimethicone, cyclopentasiloxane, dimethiconol, sodium hyaluronate, bisaccharide gum, isononyl isononoate, carnauba wax and/ or petrolatum. When present, the one or more emollients may be present in the cosmetic composition in an amount of from about 0.01% to about 20% by weight of the composition, e.g. from about 0.1% to about 10%, or about 0.5% to about 7% by weight of the composition.

The cosmetic composition may further comprise one or more emulsifiers, including but not limited to steareth-2, steareth-21, steareth-10, ceteareth-5, ceteareth-20, cetearyl glucoside, oleth-10, glyceryl stearate, polyglycerol-3 oleate, polyglyceryl-3 methylglucose distearate, sodium stearate, PEG-12 oleate, PEG-2 stearate, PEG-12 stearate, PEG-100 stearate, cetyl alcohol, cetearyl alcohol, potassium cetyl phosphate, cetearyl olivate, sorbitan olivate, PEG-80 sorbitan, sorbitan oleate, and/or sorbitan palmitate. In embodiments where one or more emulsifiers are present in the cosmetic composition, the one or more emulsifiers may be present in an amount of about 0.1% to about 10% by weight of the composition, about 0.25% to about 7.5% by weight of the composition, or about 0.5% to about 6% by weight of the composition. In one embodiment where one or more emulsifiers are present in the cosmetic composition, the one or more emulsifiers are present in an amount of about 0.5% to about 5% by weight of the composition.

The cosmetic composition of the invention may further comprise one or more surfactants, including but not limited to, anionic surfactants (e.g. sodium lauryl sulphate, sodium laureth sulphate, ammonium laureth sulphate, disodium laureth sulfosuccinate and sodium C12-15 pareth-12 carboxylate), amphoteric/zwitterionic surfactants (e.g. cocamidopropyl betaine, sodium cocoamphoacetate and cocamidopropyl hydroxysultaine), non-ionic surfactants (e.g. cocamide DEA, cocamide MEA, decyl glucoside, lauryl glucoside), and cationic surfactants (e.g. cetrimonium chloride, behentrimonium chloride and benzalkonium chloride). In embodiments where one or more surfactants are present in the cosmetic composition, the one or more surfactants may be present in an amount of from about 0.1% to about 10% by weight of the composition, e.g. from about 0.25% to about 7.5% by weight of the composition, or about 0.5% to about 6% by weight of the composition. In one embodiment where one or more surfactants are present in the cosmetic composition, the one or more surfactants are present in an amount of from about 0.5% to about 5% by weight of the composition.

The cosmetic composition of the invention may further comprise one or more preservatives, including but not limited to, 2-bromo-2nitropropane-1,3-diol (bronopol, commercially available under the trade name Myacide®), benzyl alcohol, benzoic acid, sodium benzoate, diazolidinyl urea, imidazolidinyl urea, methyl paraben, phenoxyethanol, ethyl paraben, propyl paraben, sodium methyl paraben, sodium dehydroacetate, dehydroacetic acid, polyhexamethylenebiguanide hydrochloride, isothiazolone, chlorhexidine digluconate, chlorphensin and/or sodium propyl paraben. In one embodiment, the cosmetic composition of the invention does not comprise parabens. In embodiments where one or more preservatives are present in the cosmetic composition, the one or more preservatives may be present in an amount of from about 0.001% to about 10% by weight of the composition, e.g. from about 0.01% to about 8% by weight of the composition, or about 0.1% to about 5% by weight of the composition. In one embodiment where one or more preservatives are present in the cosmetic composition, the one or more preservatives are present in an amount of from about 0.05% to about 8% by weight of the composition.

The cosmetic composition of the invention may further comprise one or more chelating agents or sequestering agents, including but not limited to, ethylenediamine tetraacetic acid (EDTA) and salts thereof (e.g. dipotassium EDTA, disodium EDTA or tetrasodium EDTA), sodium phytate, trisodium ethylene diamine disuccinate, and/or tetrasodium glutamate diacetate. In embodiments where one or more chelating agents are present in the cosmetic composition, the one or more chelating agents may be present in an amount of from about 0.001% to about 10% by weight of the composition, e.g. from about 0.01% to about 8% by weight of the composition, or about 0.1% to about 5% by weight of the composition. In one embodiment where one or more chelating agents are present in the cosmetic composition, the one or more chelating agents are present in an amount of from about 0.05% to about 8% by weight of the composition.

The cosmetic composition of the invention may further comprise one or more vitamins. For example, the cosmetic composition may further comprise vitamin B, vitamin B1 to vitamin B12, vitamin C, vitamin D, vitamin E, vitamin K, vitamin H, derivatives thereof, provitamins thereof (e.g. pro-vitamin B5 (panthenol)), or combinations thereof. In embodiments where one or more vitamins are present in the cosmetic composition, the one or more vitamins may be present in an amount of about 0.0001% to about 50% by weight of the composition, about 0.001% to about 10% by weight of the composition, about 0.01% to about 8% by weight of the composition, or about 0.1% to about 5% by weight of the composition. In one embodiment where one or more vitamins are present in the cosmetic composition, the one or more vitamins are present in an amount of from about 0.1% to about 5% by weight of the composition. In one embodiment where one or more vitamins are present, the vitamin is vitamin C and/or vitamin E.

The cosmetic composition of the invention may further comprise one or more antioxidants. These may be different to the polyphenolic antioxidant agents already present in the composition. In one embodiment where one or more such additional antioxidants are present in the cosmetic composition, the one or more additional antioxidants are present in an amount of from about 0.1% to about 5% by weight of the composition.

The cosmetic composition of the invention may further comprise one or more sunscreen agents, including but not limited to inorganic sunscreen agents (e.g. microfine titanium dioxide, microfine zinc oxide, iron oxides, talcs and/or boron nitride) and organic sunscreen agents (e.g. p-aminobenzoic acids, esters and derivatives thereof (e.g. 2-ethylhexyl p-dimethyl-aminobenzoate), methoxycinnamate esters (e.g., 2-ethylhexyl p-methoxycinnamate, 2-ethoxyethyl p-methoxycinnamate or $\alpha,\beta$-di-(p-methoxycinnamoyl)-$\alpha$'-(2ethylhexanoyl)-glycerin), benzophenones (e.g. oxybenzone), dibenzoylmethanes (e.g. 4-(tert-butyl)-4'-methoxydibenzoylmethane), 2-phenylbenzimidazole-5 sulfonic acid and salts thereof, alkyl-$\beta,\beta$-diphenylacrylates (e.g. alkyl $\alpha$-cyano-$\beta,\beta$-diphenylacrylates such as octocrylene) triazines (such as 2,4,6-trianilino-(p-carbo-2-ethylhexyl-1-oxy)-1,3,5 triazine), and/or camphor derivatives (such as methylbenzylidene camphor). In embodiments where one or more sunscreen agents are present in the cosmetic composition, the one or more sunscreen agents may be present in an amount of from about 0.01 to about 10% by weight of the composition.

The cosmetic composition of the invention may further comprise one or more pH adjusting agents, including but not limited to potassium hydroxide, sodium hydroxide, aminomethyl propanol, sodium citrate and/or triethanolamine. The cosmetic composition of the invention may have a pH from about 3 to about 10, e.g. from about 4 to about 8, or from about 5 to about 7. In embodiments where one or more pH adjusting agents are present in the cosmetic composition, the one or more pH adjusting agents may be present in an amount of from about 0.01 to about 10% by weight of the composition.

The cosmetic composition of the invention may further comprise one or more thickeners or gelling agents. For example, when the cosmetic composition is in the form of a gel, the cosmetic composition may comprise one or more thickeners or gelling agents. Examples of thickeners/gelling agents that can be used in the present invention include, but are not limited to, acrylic acid polymers (e.g. available commercially under the trade name Carbopol or Ultrez (Lubrizol), modified celluloses (e.g. hydroxyethylcellulose available commercially under the trade name Natrosol from Hercules) hydroxypropylmethyl cellulose, amine oxides, block polymers of ethylene oxide and propylene oxide (e.g. those available from BASF Wyandotte under the trade name "Pluronic"), PVM, MA, decadiene crosspolymer (e.g. available under the trade name Stabilez 60), ethoxylated fatty alcohols, salt (e.g. magnesium chloride, sodium chloride), Aristoflex AVC, phthalic acid amide, xanthan gum, sodium polyacrylate, polyvinyl alcohols, fatty alcohols, and/or alkyl galactmanans (e.g. available under the trade name N-Hance from Hercules. In embodiments where one or more thickeners/gelling agents are present in the cosmetic composition, the one or more thickeners/gelling agents may be present in an amount of about 0.01 to about 10% by weight of the composition.

The cosmetic compositions of the invention may further comprise one or more perfumes and/or colourings.

The cosmetic treatment may be for alleviating or preventing the appearance of a skin condition selected from the group consisting of skin ageing, skin elastosis, skin laxity (sagging), rhytids (wrinkles), skin inflammation, skin damage, skin burn, skin pain, muscle tightness and acne.

In the present application, the term "about" may encompass ±10%, such as ±5%, e.g. ±2% or ±1%.

The skilled person will understand that optional features of one embodiment or aspect of the invention may be applicable, where appropriate, to other embodiments or aspects of the invention.

There now follows by way of example only a description of the present invention with reference to the accompanying drawings, in which:

FIG. 1 shows a list of example cosmetic compositions according to the invention;

EXAMPLES

Interleukin-6 (IL-6) Assay

Figure 2:
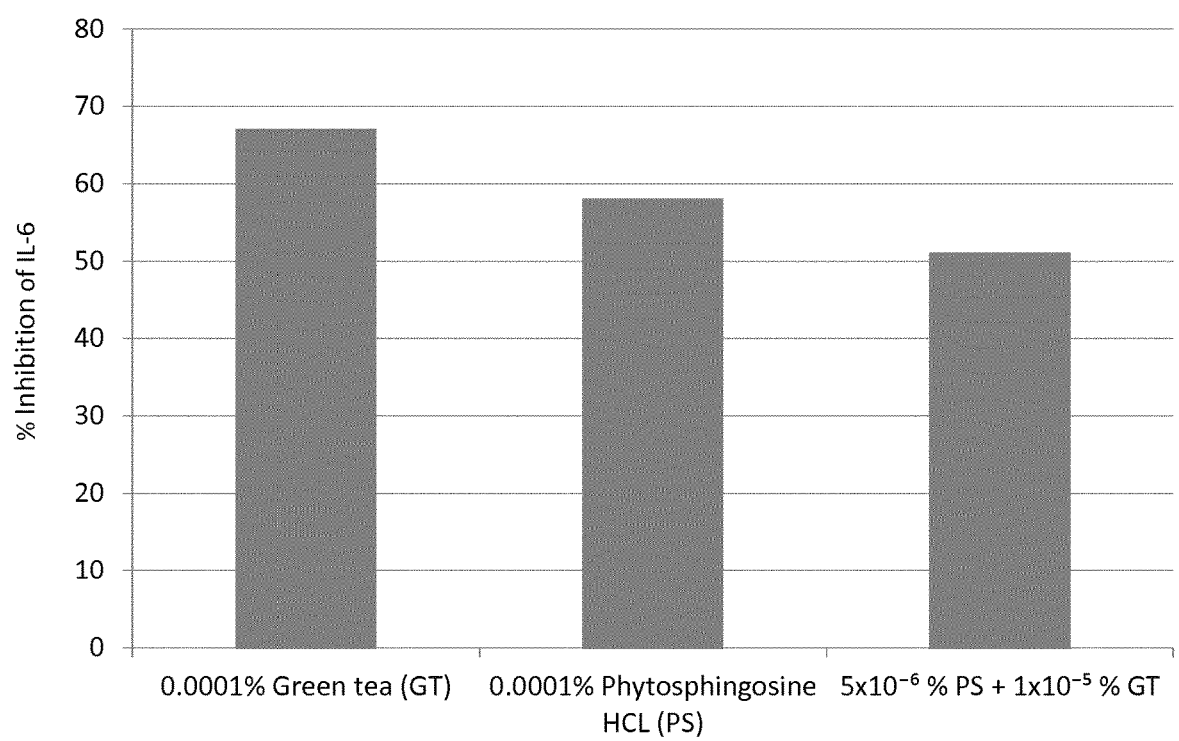
FIG. 2 is a graph comparing the IL-6 inhibition activity of individual active agents and combined active agents.

Interleukin-6 (IL-6) bioactivity in skin cells was measured. IL-6 is a cytokine and used as a biomarker for inflammation. Skin cells (keratinocytes or fibroblasts) were placed under UV stress to induce an IL-6 response in the presence of an active or blend of actives to determine the activity of that active or blend of actives in inhibiting an IL-6 response.

Skin cells (keratinocytes or fibroblasts) were taken from culture, seeded in a 96-well plate at a density of 5000 cells per well in cell growth media with supplements and left to incubate for 24 hours at 37° C. Determination of cell number for the purpose of plating was performed in accordance with standard methods known in the art.

After incubation, the cell growth media was replaced with 100 µl of PBS without calcium and magnesium and containing the relevant concentration of active(s) required. Controls include untreated irradiated and non-irradiated samples which require 100 µl pure PBS without calcium and magnesium or containing a maximum of 0.1%. Dimethyl sulfoxide (DMSO) was used where necessary to dissolve the active(s). Salicylic acid is the positive control for this assay.

The cells were incubated with the actives for 30 minutes at 37° C. before being irradiated with a UV dose of 61,500 Joules/m$^2$. The concentration of agent used in the assay is 10 to 100-fold less than the concentration of agent typically present in a cosmetic composition because this assay involved direct application of the agents onto the cells compared to the indirect contact that takes place in vivo (this is known in the art).

After irradiation, the PBS and actives were replaced with 100 µl of pre-warmed (37° C.) media without supplements and incubated for 24 hours at 37° C.

Media supernatant containing the 11-6 expressed from the cells was then collected and transferred to a fresh 96-well plate and stored at −20° C. until the ELISA was performed.

The IL-6 ELISA was performed according to the manufacturer's protocol provided with the kit and as standard in the art.

A cell viability assay was performed on remaining cells where necessary to determine the cytotoxic effects of tested actives.

Results

Compositions comprising actives were tested in accordance with the above method to determine the activity of that active or blend of actives in inhibiting an IL-6 response. In one experiment (FIG. 2), the active used was green tea, present at a concentration of 0.0001% by weight of the composition. In another experiment, the active used was phytosphingosine hydrochloride, present at a concentration of 0.0001% by weight of the composition. In another experiment (FIG. 2) compositions according to the invention were used—the actives used were a combination of green tea as the polyphenolic antioxidant agent and phytosphingosine hydrochloride as the sphingosine compound. Green tea was present in the combination at a concentration of $1 \times 10^{-5}$% by weight of the tested composition. Phytosphingosine hydrochloride was present in the combination at a concentration of $5 \times 10^{-6}$% by weight of the tested composition.

The blend of green tea and phytosphingosine hydrochloride were combined in an amount selected to achieve substantially the same level of IL-6 inhibition as when the agents were used individually. The IL-6 assay results showed that the green tea alone inhibited IL-6 activity by 67%, that phytosphingosine hydrochloride alone inhibited IL-6 activity by 58% and that the combination of green tea and phytosphingosine hydrochloride inhibited IL-6 activity by 51%. Surprisingly, the level of inhibition produced by the combination was substantially the same as when the ingredients were used individually. Therefore, despite the agents being present at significantly lower concentrations in the combination than individually, the same technical effect was still achieved.

It can be seen therefore that the percentage inhibition of the active combination is advantageously greater than the sum of the individual actives tested alone and shows synergy.

Figure 3:
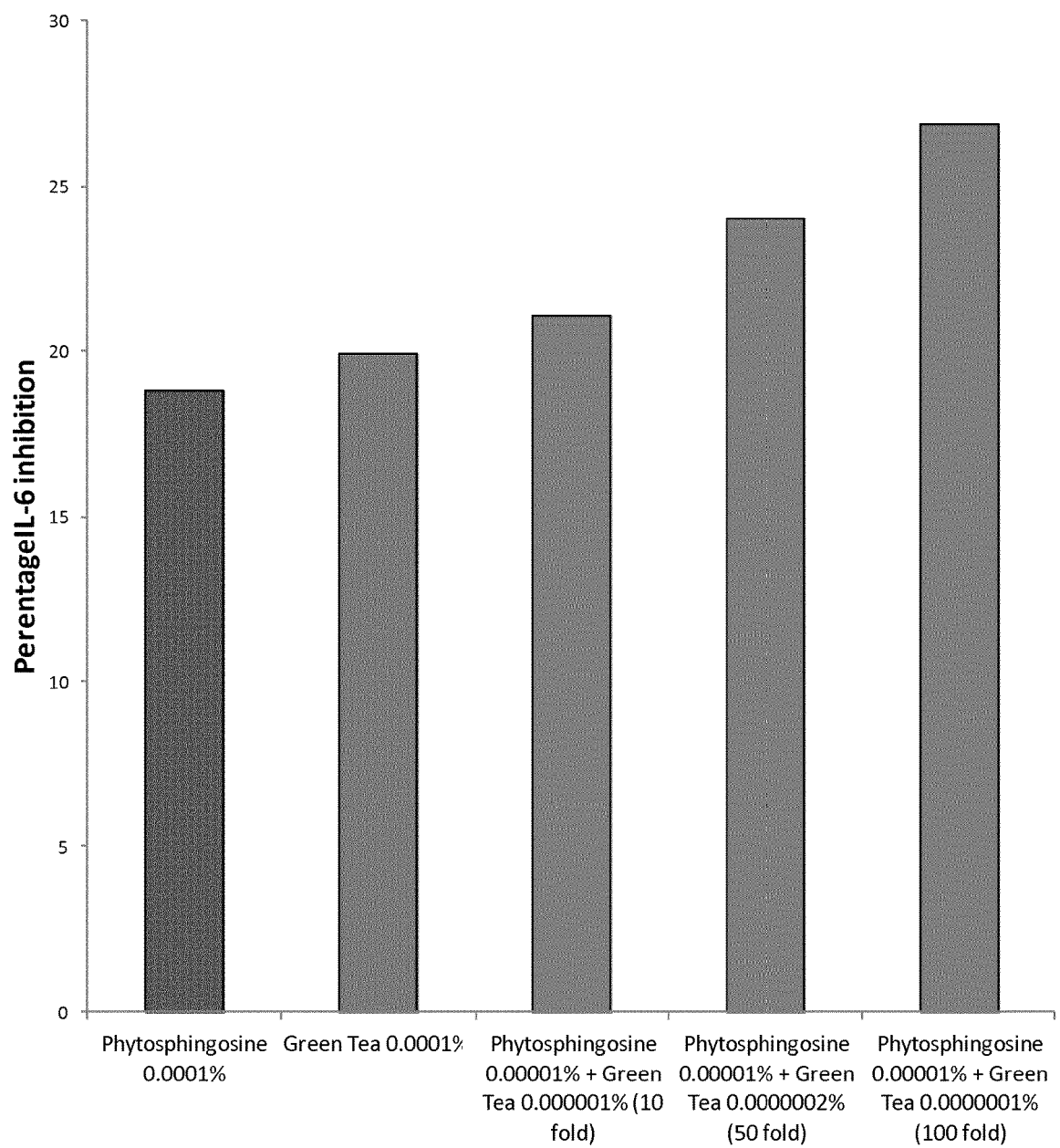
FIG. 3 is a graph comparing the IL-6 inhibition activity when exposed to phytosphingosine and green tea at varying ratios.

FIG. 3 presents IL-6 inhibition in a separate study where the phytosphingosine is present at a concentration that is either 10-fold, 50-fold or 100-fold the concentration of green tea extract (combination samples). Surprisingly a clear trend is seen where an increase in the ratio of sphingosine compound compared to polyphenolic antioxidant agent leads to an increase in IL-6 inhibition. What is especially surprising here is that the 50-fold and 100-fold examples have a greater-fold increase in the ratio as a result of decreasing green tea extract concentration rather than increasing phytosphingosine concentration. In other words, decreasing green tea extract in a phytosphingosine-containing sample (an extract shown to effectively inhibit IL-6 as shown in FIG. 3) surprisingly leads to an increase in IL-6 inhibition. This shows a novel ratio-specific synergistic effect between the sphingosine compound and the polyphenolic antioxidant agent. Note here that the concentration of phytosphingosine in the phytosphingosine only sample (0.0001%) is ten-fold greater than the phytosphingosine concentration of the combination samples and that the concentration of green tea extract in the green tea extract only sample (0.0001%) is 100-fold greater than the combination sample with the highest concentration of green tea extract (0.000001%).

It is important to note that the skin cells used in the study that led to the FIG. 3 results were different to those used in the study that led to the FIG. 2 results (differences include age of donor, the passage number of the cultured cells etc.) and so the FIG. 2 results are not directly comparable with the FIG. 3 results.

The invention claimed is:

1. A cosmetic composition comprising:
   (i) a polyphenolic antioxidant agent comprising extracts of green tea; and
   (ii) a sphingosine compound of Formula (I), or a salt or derivative thereof:

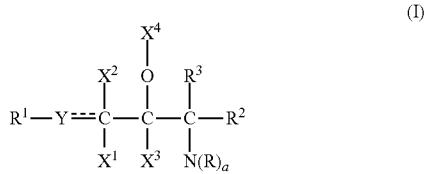

(I)

wherein:
R$^1$ is a linear, branched or cyclic, saturated or unsaturated C4-30 hydrocarbon group, which may optionally be substituted by a hydroxyl, carbonyl or amino group,
Y is any one of a methylene group (CH$_2$), a methine group (CH) and an oxygen atom,
X$^1$, X$^2$ and X$^3$ are each independently a hydrogen atom, a hydroxyl group or an acetoxy group,
X$^4$ is a hydrogen atom, an acetyl group, a glyceryl group or a substituent forming an oxo group together with the adjacent oxygen atom,
R$^2$ and R$^3$ are each independently a hydrogen atom, a hydroxyl group, a hydroxymethyl group or an acetoxymethyl group,
a is an integer which is 2 or 3, and
each R is each independently a hydrogen atom, or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups,
wherein the sphingosine compound is selected from the group consisting of phytosphingosine, phytosphingosine hydrochloride, dihydrosphingosine (sphinganine) and combinations thereof;
wherein the sphingosine compound is present in an amount 25 to 100 times the amount of the polyphenolic antioxidant agent comprising extracts of green tea, and
wherein the sphingosine compound is present in an amount of from about 0.01% to about 3% by weight of the composition.

2. The cosmetic composition of claim 1, wherein the sphingosine compound is present in an amount 40 to 80 times the amount of the polyphenolic antioxidant agent comprising extracts of green tea.

3. A method of using the cosmetic composition as defined in claim 1 by applying the cosmetic composition as a topical application on the skin.

4. The cosmetic composition of claim 1, wherein the polyphenolic antioxidant agent is present in an amount from about 0.0001% to about 2% by weight of the composition.

* * * * *